(12) United States Patent
Ishikawa et al.

(10) Patent No.: US 10,278,979 B2
(45) Date of Patent: May 7, 2019

(54) THERAPEUTIC AGENT FOR INTRACTABLE LEUKEMIA

(71) Applicant: RIKEN, Wako-Shi, Saitama (JP)

(72) Inventors: Fumihiko Ishikawa, Wako (JP); Yoriko Saito, Wako (JP)

(73) Assignee: RIKEN, Wako-Shi, Saitama (JP)

(*) Notice: Subject to any disclaimer, the term of this patent is extended or adjusted under 35 U.S.C. 154(b) by 0 days.

(21) Appl. No.: 15/556,758

(22) PCT Filed: Mar. 11, 2016

(86) PCT No.: PCT/JP2016/057795
§ 371 (c)(1),
(2) Date: Sep. 8, 2017

(87) PCT Pub. No.: WO2016/143896
PCT Pub. Date: Sep. 15, 2016

(65) Prior Publication Data
US 2018/0078567 A1 Mar. 22, 2018

Related U.S. Application Data

(60) Provisional application No. 62/131,646, filed on Mar. 11, 2015.

(51) Int. Cl.
*A61K 31/573* (2006.01)
*A61K 31/395* (2006.01)
*A61K 31/519* (2006.01)
*A61P 35/02* (2006.01)

(52) U.S. Cl.
CPC .......... *A61K 31/573* (2013.01); *A61K 31/395* (2013.01); *A61K 31/519* (2013.01); *A61P 35/02* (2018.01)

(58) Field of Classification Search
CPC .............................. A61K 31/573; A61P 35/02
See application file for complete search history.

(56) References Cited

U.S. PATENT DOCUMENTS

| | | | |
|---|---|---|---|
| 2007/0087998 A1* | 4/2007 | Ying | C07D 233/70 514/58 |
| 2009/0028933 A1 | 1/2009 | Thomas | |
| 2012/0244110 A1 | 9/2012 | Chen et al. | |
| 2015/0210698 A1 | 7/2015 | Ishikawa et al. | |

FOREIGN PATENT DOCUMENTS

| | | |
|---|---|---|
| JP | 2008-509911 A | 4/2008 |
| JP | 2014-508808 A | 4/2014 |
| WO | WO 2014/017659 A1 | 1/2014 |

OTHER PUBLICATIONS

Valentino, Stella., Expert Opin. Ther. Patents (2004) 14 (3):277-280. (Year: 2004).*

Testa, B. Biochemical Pharmacology 68 (2004) 2097-2106. (Year: 2004).*
Wolff, M. Burger's Medicinal Chemistry and Drug Discovery, fifth Edition, vol. 1. 975-977. (Year: 1995).*
Ettmayer, P. et al., Journal of Medicinal Chemistry, vol. 47, No. 10., May 6, 2004. (Year: 2004).*
Hampton, T. JAMA, Jun. 5, 2013, vol. 309, No. 21, p. 2205 (Year: 2013).*
Dordelmann, M. et al., Blood, vol. 94, No. 4 Aug. 15, 1999: pp. 1209-1217 (Year: 1999).*
Yash, Difference between lymphocyte and lymphoblast, Science & Nature (online) Jul. 25, 2014 (Year: 2014).*
Kang, B. et al., Biol. Pharm. Bull. 24(6) 701-703 (2001) (Year: 2001).*
International Search Report (Form PCT/ISA/210) for International Application No. PCT/JP2016/057795, dated Apr. 19, 2016.

(Continued)

*Primary Examiner* — Yong S. Chong
(74) *Attorney, Agent, or Firm* — Birch, Stewart, Kolasch & Birch, LLP (57) ABSTRACT

The present invention provides a therapeutic composition for intractable leukemia comprising a drug (a) and a drug (b), wherein the drug (a) is a compound represented by the following formula (I), a salt thereof, or a prodrug thereof:

[Formula 1]

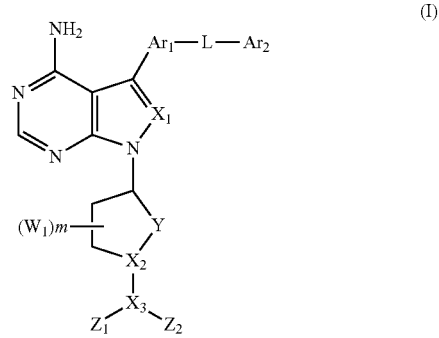

wherein, $Ar_1$ is a substituted or unsubstituted arylene group;
$Ar_2$ is a substituted or unsubstituted aryl group or a substituted or unsubstituted aralkyl group;
L is an oxygen atom, —NHCO—, or —CONH—;
$X_1$ is CH;
$X_2$ and $X_3$ are CH and a nitrogen atom, respectively;
Y is an ethylene group;
m is 0; and
$Z_1$ and $Z_2$ form a substituted or unsubstituted monocyclic heterocyclic group comprising $X_3$ and having two nitrogen atoms as ring members, and
the drug (b) is a steroidal anti-inflammatory drug; and relates to a therapy for intractable leukemia.

10 Claims, 7 Drawing Sheets

(56) References Cited

OTHER PUBLICATIONS

Saito et al., "A Pyrrolo-Pyrimidine Derivative Targets Human Primary AML Stem Cells in Vivo," Science Translational Medicine, vol. 5, Issue 181, Apr. 17, 2013, pp. 1-15 (16 pages total).
Saito et al., "Identification of Therapeutic Targets for Quiescent, Chemotherapy-Resistant Human Leukemia Stem Cells," Science Translational Medicine, vol. 2, Issue 17, Feb. 3, 2010, pp. 1-22.
Saito et al., "Induction of Cell Cycle Entry Eliminates Human Leukemia Stem Cells in a Mouse Model of AML," Nat Biotechnol, vol. 28, No. 3, Mar. 2010, pp. 1-15.

\* cited by examiner

THERAPEUTIC AGENT FOR INTRACTABLE LEUKEMIA

CROSS REFERENCE TO RELATED APPLICATIONS

This application is the National Phase of PCT International Application No. PCT/JP2016/057795, filed on Mar. 11, 2016, which claims priority under 35 U.S.C. 119(e) to U.S. Provisional Application No. 62/131,646, filed on Mar. 11, 2015, all of which are hereby expressly incorporated by reference into the present application.

TECHNICAL FIELD

The present invention relates to a therapeutic agent for intractable leukemia.

BACKGROUND ART

Most cases of leukemia are completely cured at present; however, many cases of intractable (treatment-resistant) leukemia still exist. For example, it is known that an MLL (myeloid/lymphoid or mixed-lineage leukemia) gene is located on chromosome 11 (11q23) and fuses with a gene such as AF4, AF9 and ENL through chromosomal translocation to cause leukemia. Leukemia having MLL gene rearrangement (MLL) is a typical case of intractable leukemia. MLL is known as fetal leukemia since many affected infants experience recurrence and die. The three-year survival rate is only 30% and two out of three patients die. In addition, most of MLL cases develop during infancy (up to one year old). From this, development of a therapy for MLL has been desired.

In childhood leukemia, more than half of patients experience recurrence, leading to outcome of death. To overcome the disease, many pediatricians apply currently available drugs in combination for treatment; however, it is extremely difficult to completely cure the disease.

In treatment of leukemia, the recommended therapeutic drug varies depending upon the type of leukemia and differs individually depending on the stage of treatment (remission induction therapy, maintenance therapy). For example, in a remission induction therapy for pediatric acute lymphatic leukemia, a steroidal anti-inflammatory drug such as prednisolone or dexamethasone is used.

Recently, a pharmaceutical composition having an effect for suppressing proliferation of leukemia stem cells and being effective in treating or suppressing recurrence for acute myeloid leukemia (AML) is disclosed (Patent Literature 1, and Non Patent Literature 1).

CITATION LIST

Patent Literature

Patent Literature 1: WO2014/017659

Non Patent Literature

Non Patent Literature 1: Science Translational Medicine, 2, 17ra9 (2010).

SUMMARY OF INVENTION

Technical Problem

In a case of intractable leukemia, combined use of drugs have been tried; however, it is difficult to completely cure intractable leukemia. A wide variety of therapeutic drugs and methods are present according to treatment stages; however, it is difficult to properly select them for complete cure.

The present invention was made in view of the aforementioned circumstances. An object of the invention is to provide a therapeutic composition for intractable leukemia, in particular, a therapeutic composition effective for MLL or childhood leukemia.

Solution to Problem

The present inventors repeatedly conducted studies with a view toward attaining the aforementioned object. They surprisingly found that the killing rate of leukemia cells in intractable leukemia is markedly improved by a combined use a steroidal anti-inflammatory drug, i.e., a therapeutic drug for pediatric acute lymphatic leukemia and a therapeutic drug for acute myeloid leukemia.

The present inventors conducted further detailed studies. MLL cells were transplanted to an immunodeficient mouse and treatment with a combination of dexamethasone and RK-20449 was applied. Thereafter, the MLL cells were taken from the mouse and transplanted to another immunodeficient mouse (secondary transplantation). As a result, the cell proliferation was virtually not observed. From this, they found that deeper remission (a larger number of leukemia cells can be killed) of intractable leukemia can be achieved, and reached accomplishment of the present invention.

More specifically, the present invention is summarized as follows.

(1) A therapeutic composition for intractable leukemia comprising a drug (a) and a drug (b), wherein the drug (a) is a compound represented by the following formula (I), a salt thereof, or a prodrug thereof:

[Formula 1]

wherein, $Ar_1$ is a substituted or unsubstituted arylene group;
$Ar_2$ is a substituted or unsubstituted aryl group or a substituted or unsubstituted aralkyl group;
L is an oxygen atom, —NHCO—, or —CONH—;
$X_1$ is CH;
$X_2$ and $X_3$ are CH and a nitrogen atom, respectively;
Y is an ethylene group;
m is 0; and
$Z_1$ and $Z_2$ form a substituted or unsubstituted monocyclic heterocyclic group comprising $X_3$ and having two nitrogen atoms as ring members, and
the drug (b) is a steroidal anti-inflammatory drug.

(2) The therapeutic composition for intractable leukemia, wherein the drug (a) and the drug (b) are simultaneously, separately or sequentially administered.

(3) The therapeutic composition for intractable leukemia comprising the drug (a) and the drug (b) for use in combination.

(4) The composition comprising the drug (a) for improving the therapeutic effect of the drug (b) on intractable leukemia by using the drug (b) in combination.

(5) A kit composition for treating intractable leukemia, comprising the drug (a) and the drug (b).

(6) The composition according to any one of (1) to (5), wherein the compound of the drug (a) is at least one compound selected from the group consisting of 7-[trans-4-(4-methyl-1-piperazinyl)cyclohexyl]-5-(4-phenoxyphenyl)-7H-pyrrolo[2,3-d]pyrimidin-4-amine (RK-20449) and N-(4-(4-amino-7-((trans)-4-(4-methylpiperazin-1-yl)cyclohexyl)-7H-pyrrolo[2,3-d]pyrimidin-5-yl)phenyl)-3-phenylpropanamide (RK-20693).

(7) The composition according to any one of (1) to (6), wherein the drug (b) is at least one agent selected from the group consisting of dexamethasone, prednisone, prednisolone, methylprednisolone, beclomethasone, betamethasone, fluticasone and hydrocortisone.

(8) The composition according to any one of (1) to (7), wherein the intractable leukemia is acute lymphatic leukemia.

(9) The composition according to any one of (1) to (7), wherein the acute lymphatic leukemia is MLL.

(10) The composition according to any one of (1) to (7), wherein the intractable leukemia is childhood leukemia.

(11) A method for treating intractable leukemia by simultaneously, separately or sequentially administering the drug (a) and the drug (b).

(12) The method according to (11), wherein the compound of the drug (a) is at least one compound selected from the group consisting of 7-[trans-4-(4-methyl-1-piperazinyl)cyclohexyl]-5-(4-phenoxyphenyl)-7H-pyrrolo[2,3-d]pyrimidin-4-amine (RK-20449) and N-(4-(4-amino-7-((trans)-4-(4-methylpiperazin-1-yl)cyclohexyl)-7H-pyrrolo[2,3-d]pyrimidin-5-yl)phenyl)-3-phenylpropanamide (RK-20693).

(13) The method according to (11) or (12), wherein the drug (b) is at least one agent selected from the group consisting of dexamethasone, prednisone, prednisolone, methylprednisolone, beclomethasone, betamethasone, fluticasone and hydrocortisone.

(14) The method according to any one of (11) to (13), wherein the intractable leukemia is acute lymphatic leukemia.

(15) The method according to any one of (11) to (13), wherein the acute lymphatic leukemia is MLL.

(16) The method according to any one of (11) to (13), wherein the intractable leukemia is childhood leukemia.

Advantageous Effects of Invention

Owing to the present invention, it is possible to achieve deeper remission (a larger number of leukemia cells can be killed) than that achieved by a conventional therapeutic agent or method for intractable leukemia. In consideration of a deep remission state achieved by the present invention, complete cure of intractable leukemia (for example, even after the passage of 5 years or more, the patient does not have recurrence) is expected.

BRIEF DESCRIPTION OF DRAWINGS

FIG. 1: A humanized mouse model for MLL was prepared. A key drug for MLL is a steroid (dexamethasone). The sensitivity to the steroid varied depending on each case, as indicated by broken lines. Even if once the drug seemed to work, recurrence was reproduced in the humanized mouse model. In the line graph, the horizontal axis shows time (week) and the vertical axis shows chimerism of human leukemia cells in the mouse peripheral blood.

FIG. 7 shows that MLL cells (MLL-AF9 ALL cell) in the bone marrow (BM) are eradicated by combination treatment of steroid (dexamethasone) and RK-20449. MLL cells (MLL-AF9 ALL cell) were transplanted (primary transplant) to an immunodeficient mouse. After the mouse were treated with a combination of dexamethasone and RK-20449, MLL cells were taken from the mouse and transplanted into another immunodeficient mouse (secondary transplantation). The results are shown in the graphs. The cases treated with dexamethasone alone and RK-20449 alone were used as controls (for comparison). In the secondary transplantation, MLL cells were present in significantly high percentages (cells were proliferated after transplantation) in the cases treated with a dexamethasone alone and RK-20449 alone. In the case of combination treatment, proliferation of MLL cells was virtually not observed. From this, it was shown that deeper remission (a larger number of leukemia cells can be killed) of intractable leukemia was already achieved in the stage of the primary transplantation.

DESCRIPTION OF EMBODIMENTS

The present invention will be described below.

(Therapeutic Composition)

The therapeutic composition of the present invention is a composition comprising a compound represented by the above formula (I) serving as a drug (a) and a steroidal anti-inflammatory drug serving as a drug (b) in combination.

In the formula (I), examples of the arylene group represented by $Ar_1$ include a divalent group obtained by removing one hydrogen atom on a ring carbon atom from an aryl group as described later.

Examples of the aryl group represented by $Ar_2$ include a phenyl group and a naphthyl group. Examples of the aralkyl group represented by $Ar_2$ include a benzyl group, a phenethyl group and a phenylpropyl group.

Examples of a substituent on $Ar_1$ or $Ar_2$ include a $C_{1-6}$-alkyl group such as a linear alkyl group including a methyl group, an ethyl group, a propyl group, an isopropyl group, a butyl group, an isobutyl group, a sec-butyl group, a tert-butyl group, a pentyl group, an isopentyl group and a hexyl group, and a cyclic alkyl group including a cyclopropyl group, a cyclobutyl group, a cyclopentyl group and a cyclohexyl group; a $C_{2-6}$-alkenyl group such as a vinyl group and an allyl group; a $C_{2-6}$-alkynyl group such as an ethynyl group and a propargyl group; a $C_{2-6}$-alkylene group; an aryl group such as a phenyl group and a naphthyl group; a heteroaryl group; a $C_{2-7}$-aliphatic acyl group such as an acetyl group and a propionyl group; an aromatic acyl group such as a benzoyl group; a hydroxyl group; a carbonyl group; a carboxyl group; a cyano group; a halogen atom (fluorine atom, chlorine atom, bromine atom, iodine atom); a $C_{1-6}$-alkoxy group such as a methoxy group, an ethoxy group, a propoxy group and an isopropyloxy group; an aralkyl group such as a benzyl group; an aralkyloxy group such as a benzyloxy group; a nitro group; an amino group; a $C_{1-6}$-alkylamino group; and a di($C_{1-6}$-alkyl) amino group. The $Ar_1$ or $Ar_2$ group may be substituted with a plurality of independent substituents.

Examples of the monocyclic heterocyclic group formed of $Z_1$, $Z_2$ and $X_3$ include a piperidinyl group and a piperazinyl group.

Examples of a substituent on the monocyclic heterocyclic group formed of $Z_1$, $Z_2$ and $X_3$ include a $C_{1-6}$-alkyl group, a $C_{2-6}$-alkenyl group, a $C_{2-6}$-alkynyl group, a $C_{1-3}$-alkylene group, an aryl group, a heteroaryl group, a $C_{2-7}$-aliphatic acyl group, a hydroxyl group, a carboxyl group, a cyano group, a $C_{1-6}$-alkoxy group, a hydroxy-$C_{1-6}$-alkyl group, a $C_{1-6}$-alkoxy-$C_{1-6}$-alkyl group, an aralkyl group, an aralkyloxy group, a nitro group, an amino group, a $C_{1-6}$-alkylamino group and a di($C_{1-6}$-alkyl) amino group. The heterocyclic group may be substituted with a plurality of independent substituents.

As $Ar_1$, a 1,4-phenylene group, a 2-methoxy-1,4-phenylene group, a 3-methoxy-1,4-phenylene group or a 2,5-pyridylene group is preferable.

As $Ar_2$, a phenyl group, a fluorophenyl group, a pyridyl group, a methylindolyl group or a phenethyl group is preferable; and a phenyl group, a 1-methyl-2-indolyl group or a phenethyl group is further preferable.

As L, an oxygen atom or —NHCO— is preferable.

If $X_2$ is CH and $X_3$ is a nitrogen atom, the heterocyclic group formed of $Z_1$, $Z_2$ and $X_3$ is preferably a piperazinyl group represented by the following formula (a):

[Formula 2]

wherein $R_1$ is a hydrogen atom, a $C_{1-6}$-alkyl group, a $C_{2-7}$-aliphatic acyl group, a hydroxy-$C_{1-6}$-alkyl group or a $C_{1-6}$-alkoxy-$C_{1-6}$-alkyl group; n is 0; and $X_2$ is the same as defined above.

As $R_1$ of a piperazinyl group represented by formula (a), a hydrogen atom, a methyl group, an ethyl group, a propyl group, an isopropyl group, a butyl group, an isobutyl group, a sec-butyl group, or a tert-butyl group is preferable.

As the piperazinyl group represented by formula (a), a piperazino group, a 4-methyl-1-piperazinyl group or a 4-tert-butyl-1-piperazinyl group is preferable.

If $X_2$ is a nitrogen atom and $X_3$ is CH, the heterocyclic group formed of $Z_1$, $Z_2$ and $X_3$ is preferably a group obtained by replacing the nitrogen atom binding to $X_2$ in the piperazinyl group represented by the above formula (a) with CH, and particularly preferably a piperidin-4-yl group.

As a salt of the compound represented by the above formula (I), a pharmaceutically acceptable salt is preferable, and examples thereof include a salt with an inorganic acid such as hydrochloric acid, sulfuric acid, phosphoric acid, hydrobromic acid, hydroiodic acid, nitric acid, pyrosulfuric acid and metaphosphoric acid; or an organic acid such as citric acid, benzoic acid, acetic acid, propionic acid, fumaric acid, maleic acid, tartaric acid, succinic acid, sulfonic acid (for example, methanesulfonic acid, p-toluenesulfonic acid, naphthalenesulfonic acid), an amino acid (for example, glutamic acid). If the compound represented by the above formula (I) has an acidic substituent such as a phenolic hydroxyl group or a carboxyl group, the compound can be used in the form of an alkali metal salt such as a sodium salt or a potassium salt, a lysine salt or an arginine salt.

In the specification, the "prodrug" refers to any compound as long as the compound, when administered to a living organism, generates a compound of formula (I) through a spontaneous chemical reaction, or a catalytic enzyme or a metabolic reaction. Examples of groups constituting a prodrug used for a hydroxyl group or amino group include a $C_{2-7}$-acyl group, a $C_{1-6}$-alkoxy($C_{2-7}$-acyl) group, a $C_{1-6}$-alkoxycarbonyl($C_{2-7}$-acyl) group, a $C_{1-6}$-alkoxycarbonyl group, a $C_{1-6}$-alkoxy($C_{2-7}$-alkoxycarbonyl) group, a ($C_{2-7}$-acyloxy)methyl group, a 1-($C_{2-7}$-acyloxy)ethyl group, a ($C_{2-7}$-alkoxycarbonyl) oxymethyl group and a 1-[($C_{2-7}$-alkoxycarbonyl)oxy]ethyl group, and a $C_{2-7}$-acyl group and a $C_{1-6}$-alkoxycarbonyl group are preferable. Examples of groups constituting a prodrug used for a carboxyl group include a $C_{1-6}$-alkyl group, a $C_{1-6}$-alkoxy-$C_{1-6}$-alkyl group, a ($C_{2-7}$-acyloxy)methyl group, a 1-($C_{2-7}$-acyloxy)ethyl group, a ($C_{2-7}$-alkoxycarbonyl)oxymethyl group and a 1-[($C_{2-7}$-alkoxycarbonyl)oxy]ethyl group, and a $C_{1-6}$-alkyl group and a $C_{1-6}$-alkoxy-$C_{1-6}$-alkyl group are preferable.

The details of the compounds represented by the above formula (I) and production methods thereof are described in WO2014/017659.

A compound represented by the above formula (I), a salt thereof, or a prodrug thereof (hereinafter referred to as "compound (I)") has an effect for suppressing proliferation of leukemia stem cells or an ability to kill leukemia stem cells in acute myeloid leukemia and contributes to significant improvement of a therapeutic effect of the drug (b) on intractable leukemia, in the present invention.

The drug (b) according to the present invention is a steroidal anti-inflammatory drug. The steroidal anti-inflammatory drug, which is not particularly limited, is preferably dexamethasone, prednisone, prednisolone, methylprednisolone, beclomethasone, betamethasone, fluticasone or hydrocortisone; more preferably, dexamethasone, prednisone, prednisolone or methylprednisolone; and particularly preferably dexamethasone.

According to the composition of the present invention, it is possible to achieve deeper remission (a larger number of leukemia cells can be killed) than that achieved by a conventional therapeutic agent or method for intractable leukemia. Since a deeper remission state can be achieved by the present invention, complete cure of intractable leukemia is expected. In the specification, "complete cure" refers to the state where leukemia is improved from a disease state to achieve remission and the patient does not have recurrence even after the passage of long time (for example, 5 years or more).

The therapeutic composition of the present invention may be used in combination with an auxiliary agent such as another therapeutic agent or a recurrence inhibitor for leukemia and/or an immunostimulant; however, the effect of the invention can be produced by a combination of the drug (a) and the drug (b).

The dosage forms of the drug (a) and the drug (b) can be appropriately modified by those skilled in the art.

(Therapeutic Target)

The therapeutic target of the present invention is generally a mammal. Examples of the mammal that can be mentioned include experimental animals such as rodents including a mouse, a rat, a hamster and a guinea pig, and a rabbit; farm animals such as a pig, a cow, a goat, a horse, a sheep and a mink; pet animals such as a dog and a cat; and primates such as a human, a monkey, a cynomolgus monkey, a rhesus monkey, a marmoset, an orangutan and a chimpanzee. The therapeutic target of the present invention is preferably a human.

(Target Disease)

The target disease of the present invention is intractable leukemia. In the specification, intractable leukemia also refers to treatment-resistant leukemia and includes not only leukemia whose symptoms are hardly treated by an existing drug in the initial therapy but also leukemia liable to recur. Examples of intractable leukemia include acute lymphatic leukemia (ALL) or acute myeloid leukemia (AML); are preferably acute lymphatic leukemia (ALL); and more preferably MLL (myeloid/lymphoid or mixed-lineage leukemia). MLL is leukemia characterized by the presence of leukemia cells having a variant MLL gene. Examples of the variant MLL gene include, but are not limited to, AF4, AF9 and ENL.

As another example of intractable leukemia, childhood leukemia is preferably mentioned; more preferably childhood ALL, and more preferably childhood MLL.

(Dosage and Formulation of Therapeutic Compositions)

Hereafter, the dosage and the formulation of the therapeutic composition according to the present invention are described.

The compound (I) can be administered in an as-is state or together with common pharmaceutical carriers to humans and nonhuman animals. The dosage form is not particularly limited and it is adequately selected according to need. Examples of dosage forms include: oral preparations, such as tablets, capsules, granules, fine grains, powders, controlled-release formulations, suspensions, emulsions, syrups, and elixirs; and parenteral preparations, such as injection preparations, suppositories, liniments, and adhesive skin patches.

Oral preparations are produced in accordance with conventional techniques with the use of, for example, starch, lactose, saccharose, mannite, carboxymethylcellulose, cornstarch, or inorganic salts.

In addition to the excipients described above, oral preparations can comprise binders, disintegrators, surfactants, lubricants, flowability enhancers, flavors, colorants, or aroma chemicals.

Examples of binders include starch, dextrin, powdered acacia, gelatin, hydroxypropyl starch, methylcellulose, sodium carboxymethylcellulose, hydroxypropylcellulose, crystalline cellulose, ethylcellulose, polyvinylpyrrolidone, and Macrogol.

Examples of disintegrators include starch, hydroxypropyl starch, sodium carboxymethylcellulose, carboxymethylcellulose calcium, carboxymethylcellulose, and low-substituted hydroxypropylcellulose.

Examples of surfactants include sodium lauryl sulfate, soybean lecithin, sucrose fatty acid ester, and polysorbate 80.

Examples of lubricants include talc, waxes, hydrogenated vegetable oil, sucrose fatty acid ester, magnesium stearate, calcium stearate, aluminum stearate, and polyethylene glycol.

Examples of flowability enhancers include light anhydrous silicic acid, dried aluminum hydroxide gel, synthetic aluminum silicate, and magnesium silicate.

An injection preparation is produced in accordance with a conventional technique. In general, a diluent, such as distilled water for injection, physiologic saline, aqueous glucose solution, olive oil, sesame oil, *arachis* oil, soybean oil, corn oil, propylene glycol, or polyethylene glycol, can be used. Further, a disinfectant, preservative, or stabilizer may be added, according to need. From the viewpoint of safety, a vial or another container may be filled with an injection preparation, the resultant may be frozen, moisture may be removed via a conventional lyophilization technique, and a solution may then be prepared from the lyophilization product immediately before use. Furthermore, an isotonizing agent, stabilizer, preservative, soothing agent, or the like may be added, according to need.

Examples of other forms of parenteral preparations include liquid preparations for external use, liniments, such as ointments, adhesive skin patches, and suppositories for intrarectal administration. Parenteral preparations are produced in accordance with conventional techniques.

The preparation of the present invention can be administered at a frequency of once to several instances every day to once to several instances every week to month, although the frequency of administration varies in accordance with the dosage form, the route of administration, and other conditions.

In order to achieve desirable efficacy of oral preparations, in general, it is suitable for an adult to take 1 to 200 mg of the compound (I) in several separate instances per day, although the dosage varies depending on, for example, age, body weight, and severity of symptoms of a patient.

In order to achieve desirable efficacy of parenteral preparations, in general, it is adequate for an adult to take 1 to 50 mg of the compound (I) per day by means of intravenous injection, intravenous drip infusion, subcutaneous injection, or intramuscular injection, although the dosage varies depending on, for example, age, body weight, and severity of symptoms of a patient.

The dosage of a steroidal anti-inflammatory drug is not particularly limited as long as the drug provides a medicinal effect. According to the present invention, the steroidal anti-inflammatory drug produces a synergistic effect if it is used in combination with compound (I). Thus, the steroidal anti-inflammatory drug can be used in a dose lower than that usually used.

Compound (I) serving as the drug (a) is administered in combination with a steroidal anti-inflammatory drug serving as the drug (b). As the method, both drugs may be added in a single preparation or in two separate preparations and administered, simultaneously, separately or sequentially, if necessary, at a predetermined interval.

Note that, the contents of all publications including the specifications of patents and patent applications cited herein are incorporated herein by reference in their entirety within the ranges of the disclosures.

Example

The present invention will be more specifically described by way of Example; however, the range of the present invention is not limited by the following Example.

(Materials and Methods)

NOD. Cg-Prkdc$^{scid}$ Il2rg$^{tm1Wjl}$/Sz (NOD/SCID/IL2rg$^{null}$, NSG) mice were developed by subjecting a complete null mutation in the Il2rg gene locus to back cross with NOD. Cg-Prkdc$^{scid}$ (NOD/SCID) lineage, in the Jackson Laboratory (Bar Harbor, Me. state, USA) (Shultz, L. D. et al., Multiple defects in innate and adaptive immunologic function in NOD/LtSz-scid mouse. J. Immunol. 154, 180-191 (1995)). The mice were raised by feeding irradiated food and acidified water in the animal facilities of RIKEN and the Jackson Laboratory in accordance with the guideline established by the Institutional Animal Committees and maintained under bacterial flora specified.

NSG mice in the neonatal period were exposed to radiation (1.5 G) and then patient-derived MLL cells (MLL-AF9) were transplanted to the mice. After the presence of the human leukemia cells in the peripheral blood was confirmed by flow cytometry based on the presence of hCD45+CD19+, treatment of the mice (leukemia humanized mice) with dexamethasone (70 mg/kg IP daily) and/or RK-20449 (30 mg/kg IP BID, twice a day) or both was started.

After the treatment, the mice were euthanized and the appearance frequency of human leukemia cells in the bone marrow was determined by flow cytometry. At the same time, one of the femur bones was fixed in PFA and 5 uM-thin sections were prepared. The thin sections were stained with an antibody against hCD45 and DAB to show localization of human leukemia cells (stained brown).

Figure 1:
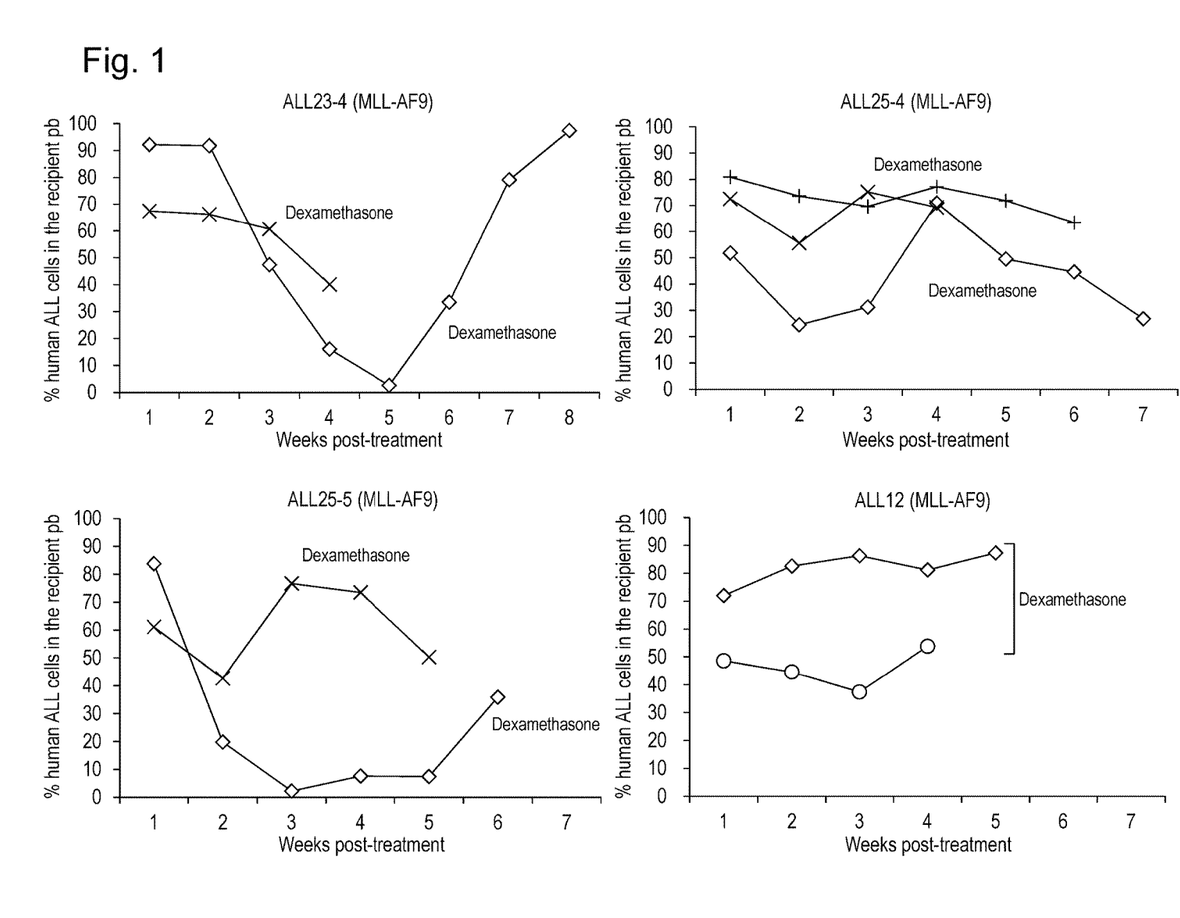

One of the key drugs against the leukemia is a steroid (dexamethasone). Sensitivity to the steroid varies depending on the case, as indicated by broken lines of FIG. 1. Even if once a drug seemed to work, recurrence was reproduced in the humanized mouse model (FIG. 1).

Figure 2:
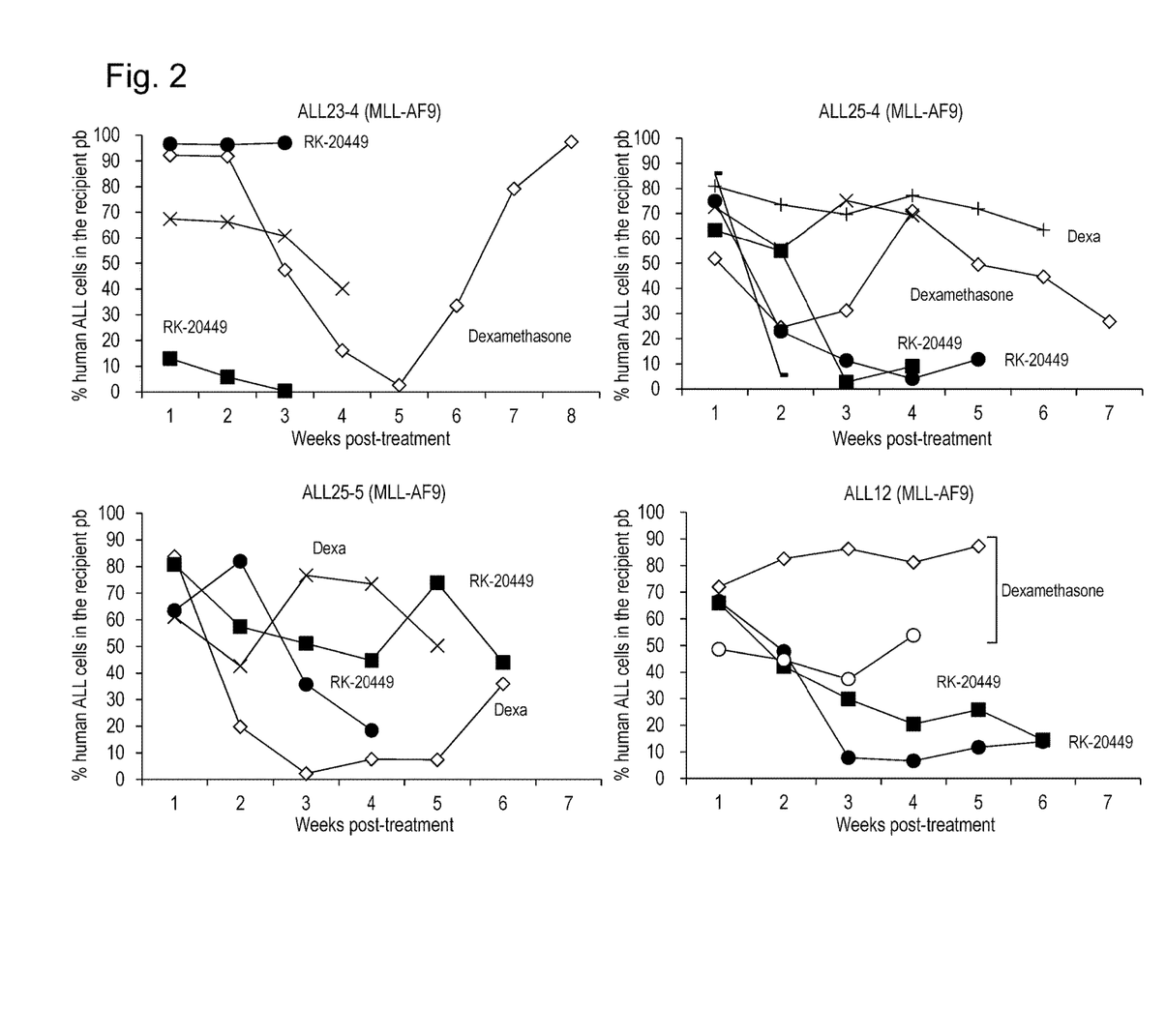
FIG. 2: In the line graph, the horizontal axis shows time (week) and the vertical axis shows chimerism of human leukemia cells in the mouse peripheral blood. As disclosed in WO2014/017659, the effectiveness of compounds inhibiting HCK and FLT3 on adult AML has been found. Even if one of the compounds, RK-20449, is used, it is not easy to eradicate MLL by single use, as indicated by broken lines.

As disclosed in WO2014/017659, the effectiveness of compounds inhibiting HCK and FLT3 on adult AML has been found. One of the compounds is RK-20449. As indicated by broken lines in FIG. 2, it is not easy to eradicate MLL by single use of RK-20449 (FIG. 2).

Figure 3:
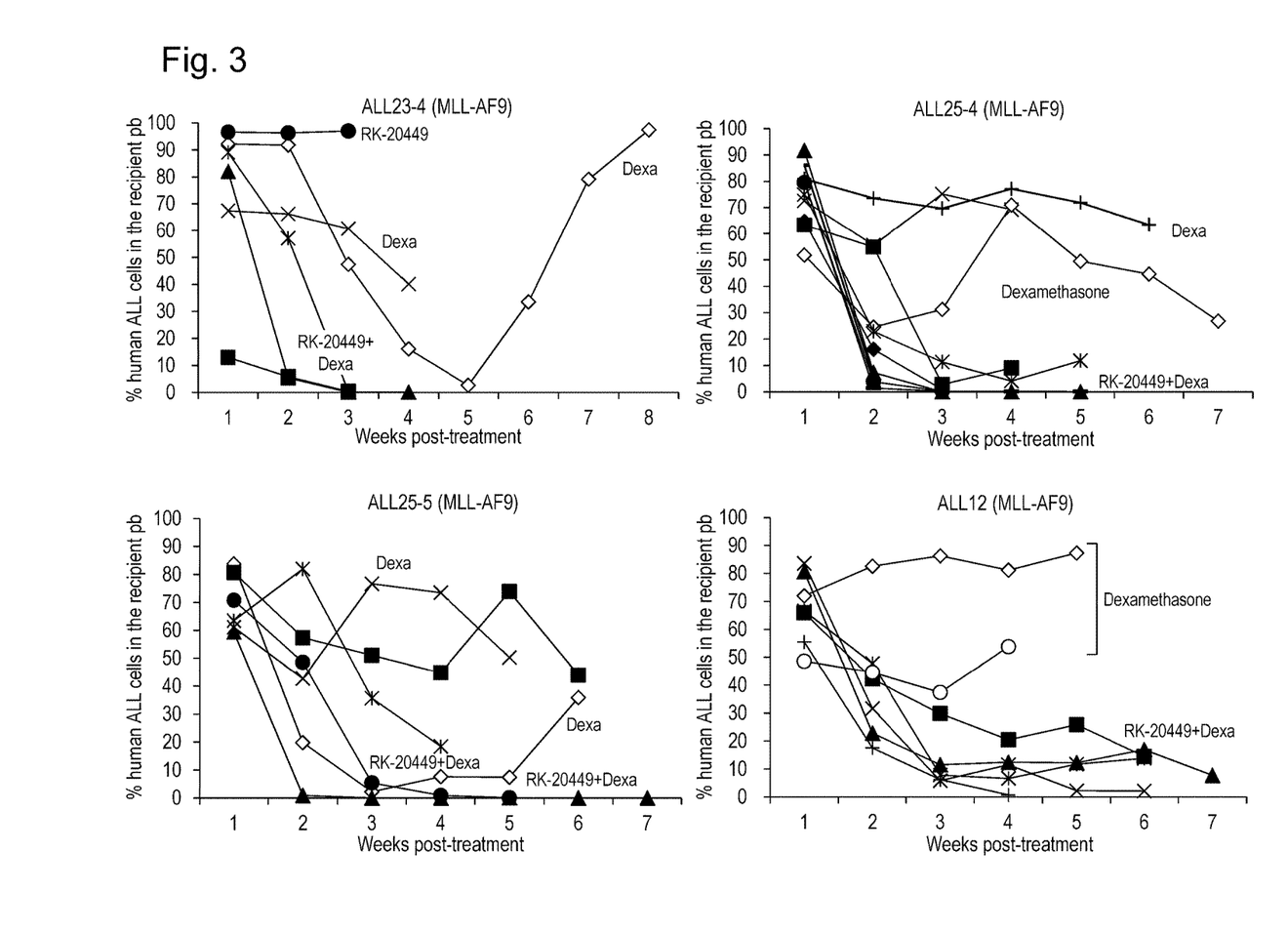
FIG. 3: In the line graph, the horizontal axis shows time (week) and the vertical axis shows chimerism of human leukemia cells in the mouse peripheral blood. It was impossible to expect complete cure of MLL by single use of a steroid (dexamethasone) or RK-20449; however, when steroid and RK-20449 were used in combination, remarkable medicinal effects were observed in all four cases shown herein. The vertical axis shows the percentage of human leukemia cells in the peripheral blood. The percentage is almost zero in all cases.

It is impossible to expect complete cure of MLL by a steroid (dexamethasone) alone or RK-20449 alone; however, a combined use of steroid+RK-20449 produced a significant medicinal effect in all four MLL-AF9 cases shown herein. The vertical axis in FIG. 3 shows the percentage of human leukemia cells in the peripheral blood. The percentage is almost zero in all cases (FIG. 3).

The leukemia cells of other types of MLL, i.e., MLL-ENL and MLL-AF4, and leukemia (MLL-negative leukemia) that developed in an infant, were taken and transplanted to NSG mice in the same manner as above. After emergence of human leukemia cells in the mouse peripheral bloods was confirmed, the same treatment as above was applied. The effect of a combined use of a steroid and RK-20449 was examined based on chimerism of human leukemia cells in blood. As a result, similarly to the case of MLL-AF9, the combined use of a steroid and RK-20449 is confirmed to have a significant ability (effect) to kill leukemia cells.

Figure 4:
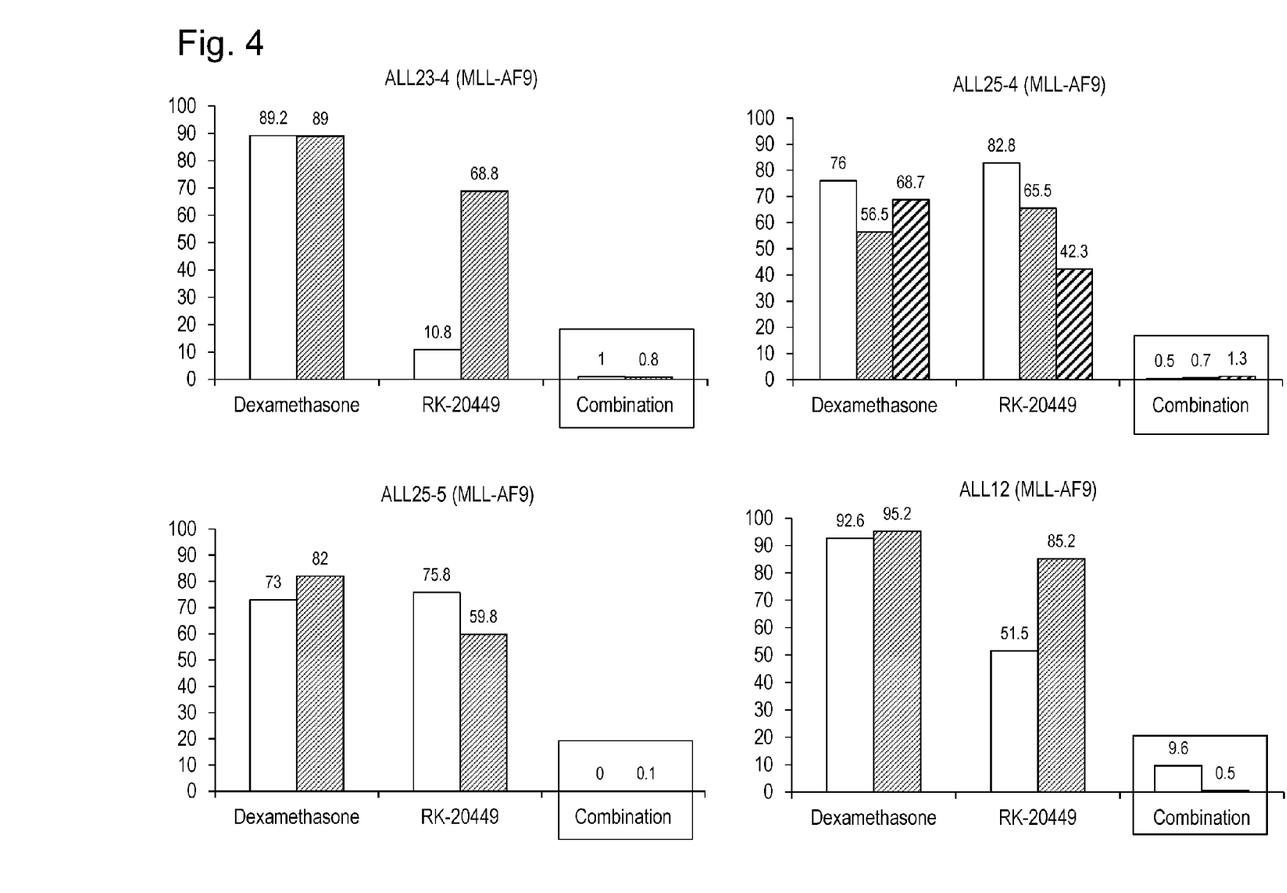
FIG. 4 shows that MLL cells (MLL-AF9 ALL cell) in the bone marrow (BM) were eradicated by combination treatment of a steroid (dexamethasone) and RK-20449. When the medicinal effect was examined in the bone marrow as well as in the peripheral blood, the therapeutic effects obtained by single use of the agents were not sufficient but the medicinal effect obtained by a combination use of them was strong. The medicinal effect is not conceivable be equal to the sum of the medicinal effects of the steroid and RK-20449, and a synergistic effect is considered to be present.

Following the examination of the medicinal effect in the peripheral blood, the medicinal effect was examined in the bone marrow in the leukemia humanized mouse of the MLL-AF9 case. A sufficient therapeutic effect was not obtained by treatment with individual agents alone; however, a strong medicinal effect was observed by a combined use thereof (FIG. 4). The medicinal effect is not conceivable to be equal to the sum of the medicinal effects of a steroid and RK-20449 and a synergistic effect is considered to be present.

Figure 5:
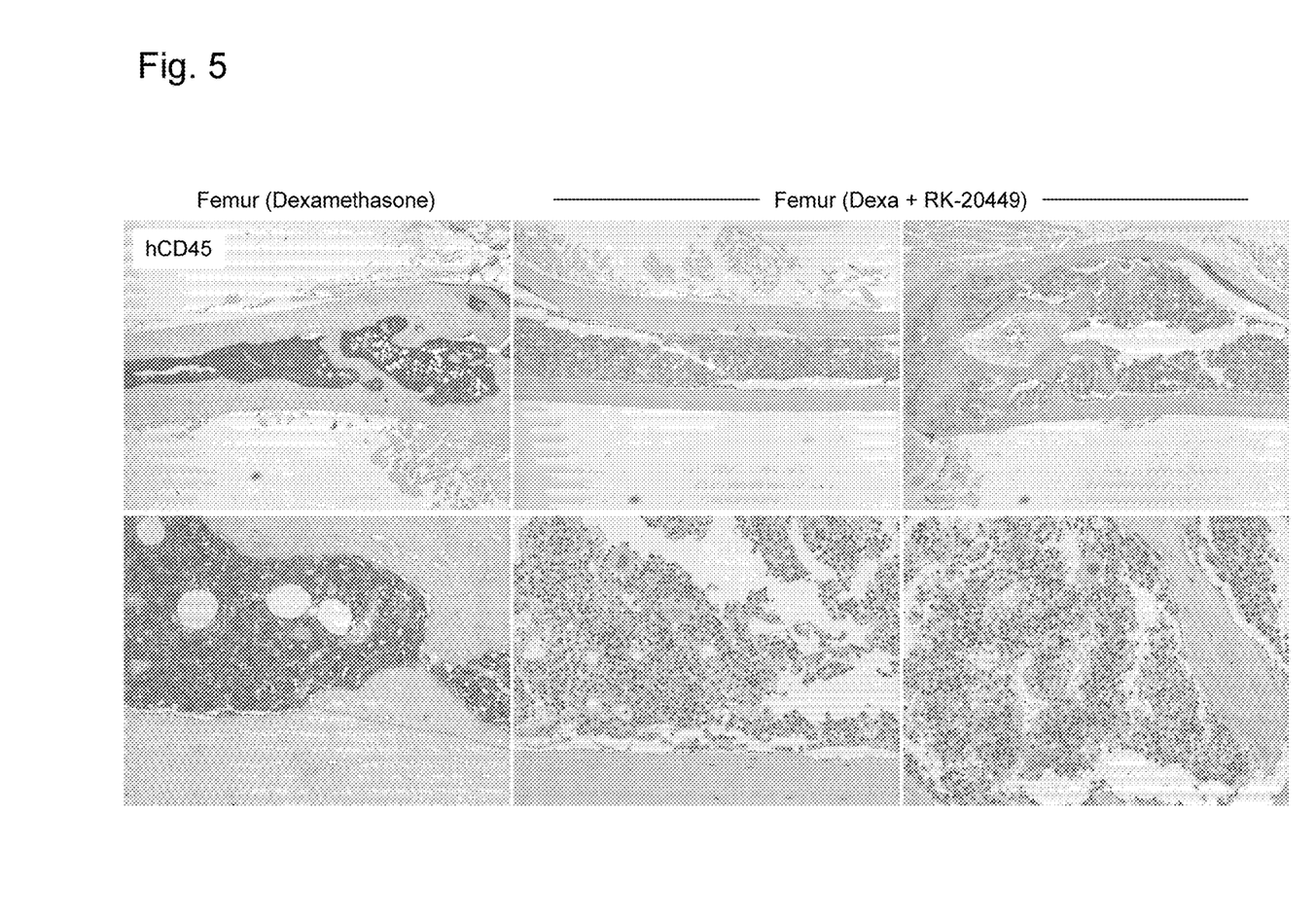
FIG. 5 shows that MLL cells (MLL-AF9 ALL cell) in the bone marrow (BM) are eradicated by combination treatment of steroid (dexamethasone) and RK-20449. Photographs of stained bone marrow of a leukemia humanized mouse after treatment are shown. A large number of human leukemia cells stained brown are present in the bone marrow after administration of a steroid alone, as shown herein; however, with the combination therapy, leukemia cells stained brown are virtually not present, as shown on the right.

After administration of a steroid alone, a large number of human leukemia cells (stained brown) are present in the bone marrow as mentioned above. However, with the combination therapy, leukemia cells stained brown are virtually not present, as shown on the right (FIG. 5).

Figure 6:
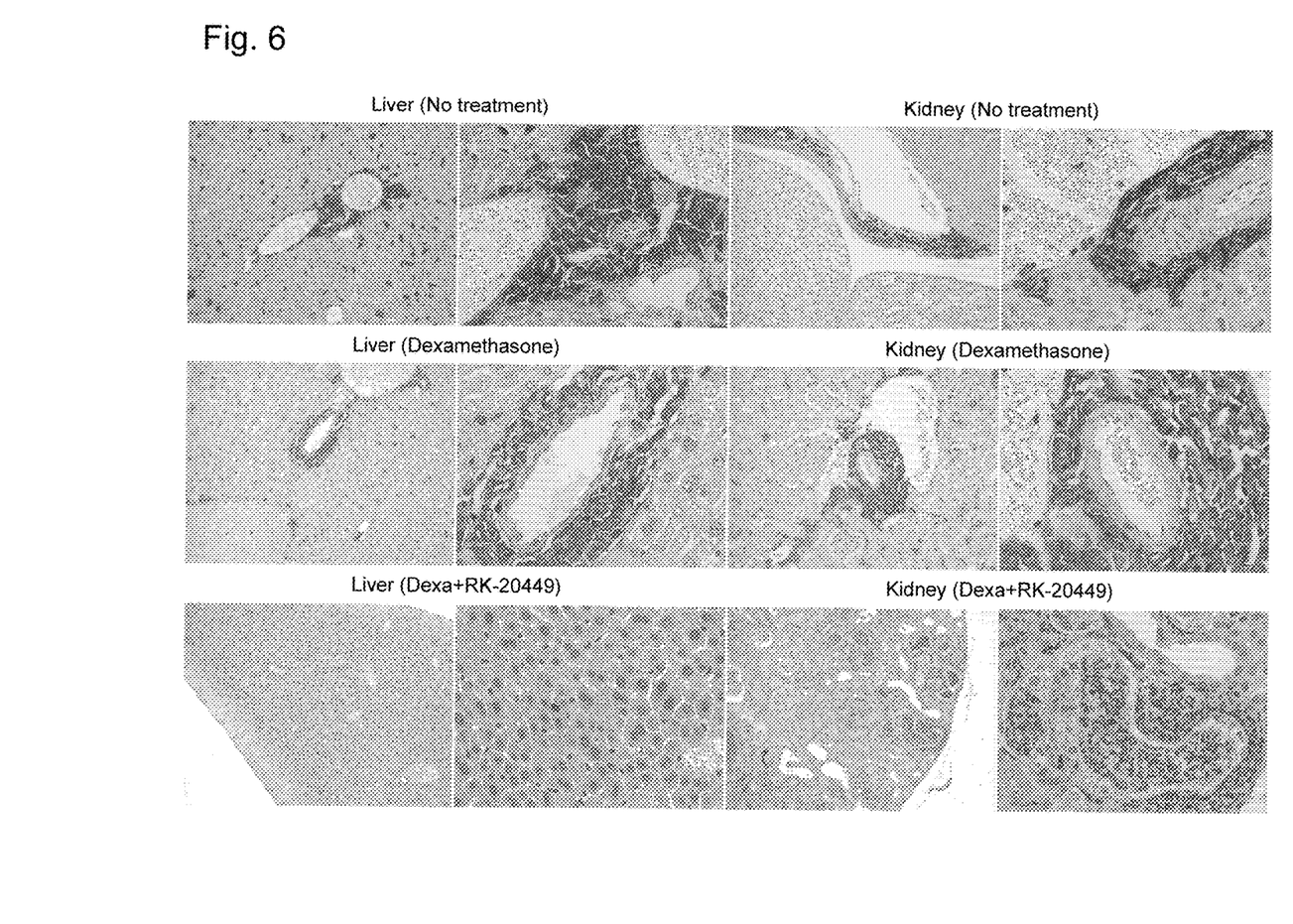
FIG. 6 shows photographs of the liver and kidney of a leukemia humanized mouse after treatment. The invasion observed there cannot be dramatically improved by the steroid, which has been used as a conventional key drug; however, it was found that leukemia cells invading not only in the bone marrow but also in the liver and kidney can be killed by steroid+RK-20449

A conventional key drug, a steroid, is not enough to dramatically improve invasion of leukemia cells; however, it was found that leukemia cells that invade not only in the bone marrow but also in the liver and the kidney can be killed by steroid+RK-20449 (FIG. 6).

Finally, human leukemia cells remaining in the bone marrow were purified by sorting and transplanted to neonatal NSG mice (secondary transplantation).

Figure 7:
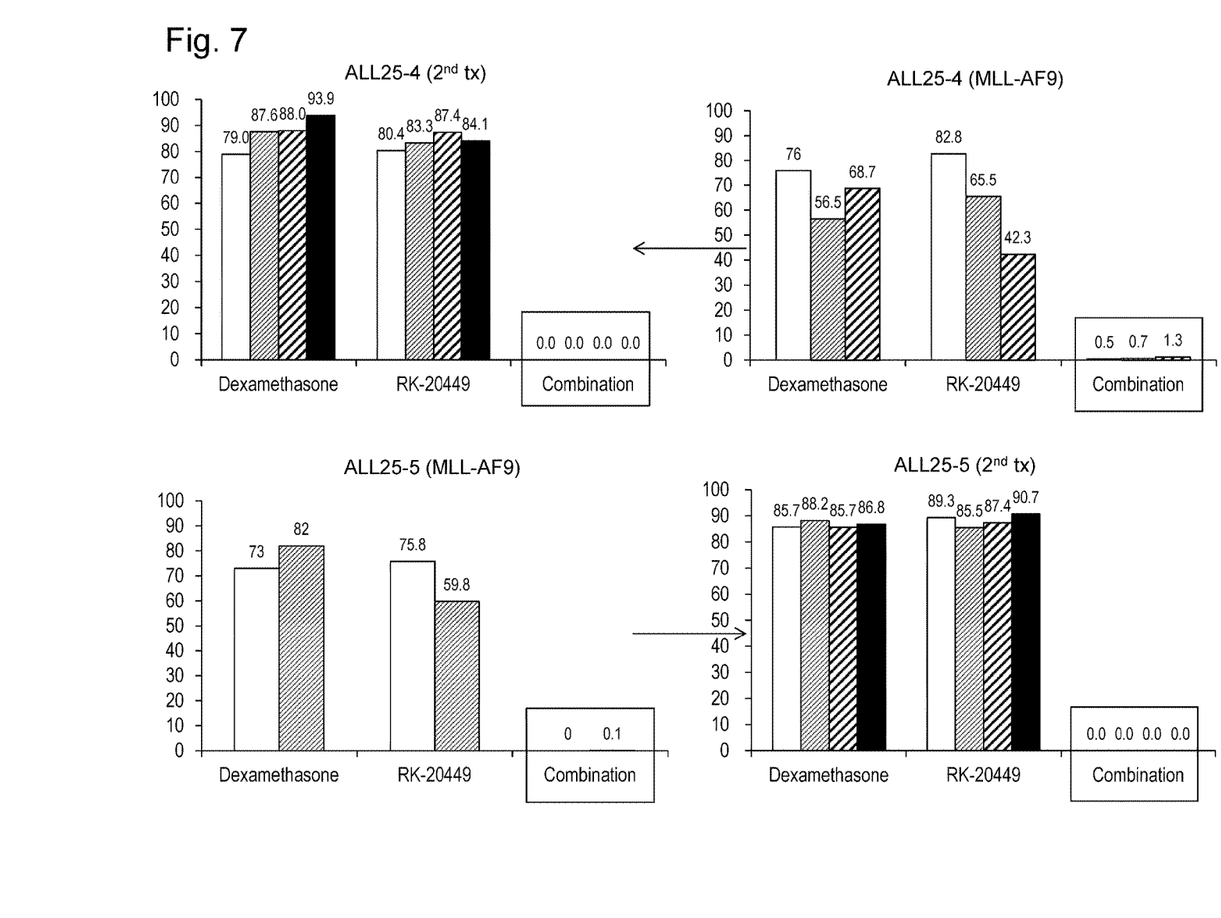

MLL cells (MLL-AF9 ALL cells) were transplanted (primary transplant) to an immunodeficient mouse and a treatment with a combination of dexamethasone and RK-20449 was applied. Thereafter, MLL cells were taken from the mouse and transplanted to another immunodeficient mouse (secondary transplantation). The results are shown in the graphs as FIG. 7. The cases treated with dexamethasone alone and RK-20449 alone were used as controls (for comparison). In the secondary transplantation cases treated with dexamethasone alone and RK-20449 alone, MLL cells were present in significantly high percentages (cells were proliferated after transplantation); however, with the combination treatment, proliferation of MLL cells was virtually not observed. From this, it was found that deeper remission (a larger number of leukemia cells can be killed) of intractable leukemia was already achieved in the stage of the primary transplantation.

The invention claimed is:

1. A therapeutic composition for intractable leukemia comprising a drug (a) and a drug (b), wherein the drug (a) is 7-[trans-4-(4-methyl-1-piperazinyl)cyclohexyl]-5-(4-phenoxyphenyl)-7H-pyrrolo[2,3-d]pyrimidin-4-amine (RK-20449) or a salt thereof, and the drug (b) is dexamethasone.

2. A composition comprising the drug (a) according to claim 1, for improving a therapeutic effect of the drug (b) on intractable leukemia by using the drug (b) in combination.

3. A kit composition for treating intractable leukemia, comprising 7-[trans-4-(4-methyl-1-piperazinyl)cyclohexyl]-5-(4-phenoxyphenyl)-7H-pyrrolo[2,3-d]pyrimidin-4-amine (RK-20449) or a salt thereof, and dexamethasone.

4. The composition according to claim 1, wherein the intractable leukemia is acute lymphatic leukemia.

5. The composition according to claim 1, wherein the intractable leukemia is MLL.

6. The composition according to claim 1, wherein the intractable leukemia is childhood leukemia.

7. A method for treating intractable leukemia by simultaneously, separately or sequentially administering 7-[trans-4-(4-methyl-1-piperazinyl)cyclohexyl]-5-(4-phenoxyphenyl)-7H-pyrrolo[2,3-d]pyrimidin-4-amine (RK-20449) or a salt thereof, and dexamethasone.

8. The method according to claim 7, wherein the intractable leukemia is acute lymphatic leukemia.

9. The method according to claim 7, wherein the intractable leukemia is MLL.

10. The method according to claim 7, wherein the intractable leukemia is childhood leukemia.

* * * * *